(12) United States Patent
Asano et al.

(10) Patent No.: US 11,510,643 B2
(45) Date of Patent: Nov. 29, 2022

(54) CALIBRATION METHOD AND APPARATUS FOR MEASUREMENT X-RAY CT APPARATUS, MEASUREMENT METHOD AND APPARATUS USING THE SAME, AND MEASUREMENT X-RAY CT APPARATUS

(71) Applicant: MITUTOYO CORPORATION, Kanagawa (JP)

(72) Inventors: Hidemitsu Asano, Kanagawa (JP); Masato Kon, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 134 days.

(21) Appl. No.: 17/024,061

(22) Filed: Sep. 17, 2020

(65) Prior Publication Data

US 2021/0085279 A1 Mar. 25, 2021

(30) Foreign Application Priority Data

Sep. 20, 2019 (JP) .............................. JP2019-172253

(51) Int. Cl.
*A61B 6/00* (2006.01)
*A61B 6/03* (2006.01)
*A61B 6/04* (2006.01)

(52) U.S. Cl.
CPC .............. *A61B 6/583* (2013.01); *A61B 6/032* (2013.01); *A61B 6/0407* (2013.01)

(58) Field of Classification Search
CPC ....... A61B 6/583; A61B 6/032; A61B 6/0407; A61B 6/582; G01N 23/046; G01N 2223/303
See application file for complete search history.

(56) References Cited

U.S. PATENT DOCUMENTS

2013/0230150 A1* 9/2013 Weiss ...................... G01T 7/005
378/207

FOREIGN PATENT DOCUMENTS

JP 2002-71345 3/2002
JP 2004-12407 1/2004

\* cited by examiner

*Primary Examiner* — Courtney D Thomas
(74) *Attorney, Agent, or Firm* — Greenblum & Bernstein, P.L.C.

(57) ABSTRACT

Volume data is generated by performing a CT scan with a spherical calibration jig having known dimensions in contact with an object. A profile of the surface shape of the object in the volume data is obtained, and a boundary surface of the spherical calibration jig is calculated from the center coordinates of the spherical calibration jig. A correction value for adjusting a boundary surface of the object determined from the gradient of the profile to the boundary surface of the spherical calibration jig is determined, and the boundary surface of the object is corrected by using the correction value. The shape of the object is determined by using the corrected boundary surface. The precision of measurement X-ray CT can thus be increased by accurately detecting the boundary surface of the object.

12 Claims, 7 Drawing Sheets

CALIBRATION METHOD AND APPARATUS FOR MEASUREMENT X-RAY CT APPARATUS, MEASUREMENT METHOD AND APPARATUS USING THE SAME, AND MEASUREMENT X-RAY CT APPARATUS

CROSS-REFERENCE TO RELATED APPLICATION

The disclosure of Japanese Patent Application No. 2019-172253 filed on Sep. 20, 2019 including specifications, drawings and claims is incorporated herein by reference in its entirety.

TECHNICAL FIELD

The present invention relates to a calibration method and apparatus for a measurement X-ray CT apparatus, a measurement method and apparatus using the same, and a measurement X-ray CT apparatus. In particular, the present invention relates to a calibration method and apparatus for a measurement X-ray CT apparatus, a measurement method and apparatus using the same, and a measurement X-ray CT apparatus that can achieve high precision by accurately detecting a boundary surface of an object.

BACKGROUND ART

Medical X-ray CT apparatuses were put to practical use in the 1970s. On the basis of the technique, X-ray CT apparatuses intended for industrial products appeared in the early 1980s. Since then, industrial X-ray CT apparatuses have been used to observe and inspect voids in casting parts, welding defects in welded parts, and defects in circuit patterns of electronic circuit parts, which are difficult to identify from external appearance. In the meantime, the prevalence of 3D printers in recent years is boosting demand for not only observation and inspection inside workpieces produced by 3D printers but also 3D dimension measurement of internal structures and higher precision thereof.

In view of the foregoing technical trend, measurement X-ray CT apparatuses are becoming prevalent, especially in Germany (see Japanese Patent Application Laid-Open Nos. 2002-71345 and 2004-12407). In such measurement X-ray CT apparatuses, an object to be measured is placed at the center of a rotating table, and X-ray irradiation is performed while rotating the object to be measured.

FIG. 1 shows a configuration of a typical X-ray CT apparatus 1 used for measurement. An X-ray source 12, an X-ray detector 14, a rotating table 16, and an XYZ moving mechanism unit 18 are accommodated in an enclosure 10 for blocking X-rays. The X-ray source 12 emits X-rays 13 in the form of a cone beam. The X-ray detector 14 detects the X-rays 13. An object W is placed on the rotating table 16. The rotating table 16 rotates the object W for CT imaging. The XYZ moving mechanism unit 18 is intended to adjust the position and magnification of the object W projected on the X-ray detector 14. The X-ray CT apparatus 1 further includes a controller 20 that controls such devices, and a control PC 22 that gives instructions to the controller 20 on the basis of user operations.

Aside from various device controls, the control PC 22 has a function of displaying a projection image of the object W projected on the X-ray detector 14, and a function of reconstructing a tomographic image from a plurality of projection images of the object W.

As shown in FIG. 2, the X-rays 13 emitted from the X-ray source 12 are transmitted through the object W on the rotating table 16 and reach the X-ray detector 14. The X-ray detector 14 obtains transmission images (projection images) of the object W in all directions as the object W is rotated. A tomographic image of the object W is generated by reconstructing the projection images by using a reconstruction algorithm such as back projection and iterative reconstruction.

The position of the object W can be moved by controlling X-, Y-, and Z-axes of the XYZ moving mechanism unit 18 and a θ-axis of the rotating table 16. The imaging range (position and magnification) and imaging angle of the object W can thus be adjusted.

To obtain a tomographic image or volume data of the object W (stereoscopic image or a set of tomographic images of the object W in the Z-axis direction), which is the ultimate goal of the X-ray CT apparatus 1, a CT scan is performed on the object W.

A CT scan includes two processes, namely, acquisition of projection images of the object W and CT reconstruction. In the projection image acquisition process, the rotating table 16 on which the object W is placed is continuously rotated at a constant speed or intermittently rotated in constant step widths during X-ray irradiation, whereby projection images of the object W are obtained in all directions around (at constant intervals). CT reconstruction is performed on the obtained projection images in all directions around (at constant intervals) by using a CT reconstruction algorithm such as back projection and iterative reconstruction. A tomographic image or volume data of the object W is thereby generated as illustrated in FIG. 3.

To measure an object by using a measurement X-ray CT apparatus, a CT scan is initially performed to obtain volume data on the object as described above. After a surface shape is detected from the volume data, various measurements are performed on the surface shape.

SUMMARY OF INVENTION

Technical Problem

However, in the foregoing process, the boundary of the surface shape is difficult to correctly detect because of characteristics of the X-ray source and the X-ray detector, and there has been a problem that the measurement accuracy is significantly affected by the surface shape.

The present invention has been made in order to solve the above-described problem in the conventional technique, and is directed to increasing the precision of measurement X-ray CT by measuring a spherical calibration jig having known dimensions along with an object to accurately detect the boundary surface of the object.

Solution to Problem

A surface shape (boundary surface) in volume data has a curved profile with some width as shown in FIG. 4. A boundary surface close to the true value is difficult to detect from such a profile.

However, as shown in FIG. 5, volume data on a sphere (perfect sphere) 30 made of a single material shows a spherical surface shape of uniform profile in any place (if corrections related to X-ray have been applied). The center coordinates of the sphere can thus be determined with considerable accuracy regardless of which position on a profile is assumed as the boundary surface.

In view of the foregoing, in the present invention, the boundary surface of an object is accurately detected by performing a CT scan with a sphere of a single material having known dimensions (hereinafter, spherical calibration jig) in contact with the object to obtain volume data thereon.

As described above, the center coordinates of the spherical calibration jig can be accurately determined. Since the dimensions of the spherical calibration jig are known, the boundary surface of the spherical calibration jig can also be accurately determined.

To accurately detect the boundary surface of an object W, as shown in FIG. 6, the contact point between the object W and the spherical calibration jig 30 needs to be correctly determined. A contact direction needs to be determined for that purpose.

To detect a boundary surface, the user selects which boundary surface to detect, for example, on the basis of the material of the object W. In selecting the boundary surface to be detected, an approximate direction where the boundary surface is can be determined. The contact direction (in FIG. 6, horizontal direction) can be determined by using the information about the approximate direction. With the approximate direction determined by the user's selection of the boundary surface as a search reference direction, the presence or absence of a contact is determined by checking profiles while shifting directions around the search reference direction.

For example, as shown in FIG. 7, vectors starting at the center coordinates of the spherical calibration jig 30, extending in directions slightly shifted from the search reference direction will be denoted by A, B, and C. The resulting profiles show components corresponding to the spherical calibration jig 30, an air layer (if any), and the object W in order along the directions of the respective vectors. Since a vector along which there is no air layer between the spherical calibration jig 30 and the object W can be said to be the condition for contact, the vicinity of the boundary surface of the spherical calibration jig 30 is checked for the absence of an air layer. An air layer transmits X-rays more easily than the spherical calibration jig 30 and the object W, and thus appears as a low profile component. The vector along which the profile component near the boundary surface of the spherical calibration jig 30 is the highest among the vectors A, B, and C can therefore be said to be close to the contact direction.

In such a manner, a desired profile is searched for around the search reference direction, whereby a search direction of high precision is determined to calculate a contact point.

To accurately determine the boundary surface of the object W by using the contact point determined as described above, boundary surfaces determined from the gradients or the like of the profiles are used as shown in FIG. 8. A difference between the contact point determined by using the spherical calibration jig 30 and the contact point determined from the gradient of a profile can be used as a correction value. The correction value determined from the prolife in the contact direction (contact point) can be applied to part or all of the boundary surface of the same object (same material).

The spherical calibration jig 30 may be made of a material such as a resin, aluminum, and iron. The spherical calibration jig 30 can be selected as appropriate on the basis of the X-ray measurement conditions (such as tube voltage and tube current) during a CT scan and the material of the object W.

The present invention has been achieved on the basis of the foregoing findings, and solves the foregoing problem by the provision of a calibration method for a measurement X-ray CT apparatus configured to irradiate an object placed on a rotating table with X-rays while rotating the object, and reconstruct a projection image of the object to generate a tomographic image of the object. The method includes: generating volume data by performing a CT scan with a spherical calibration jig having a known dimension in contact with the object; obtaining a profile of a surface shape of the object in the volume data, and calculating a boundary surface of the spherical calibration jig from center coordinates of the spherical calibration jig; and determining a correction value for adjusting a boundary surface of the object determined from a gradient of the profile to the boundary surface of the spherical calibration jig.

Here, the spherical calibration jig may be made of the same material as that of the object.

The present invention also solves the foregoing problem by the provision of a calibration apparatus for a measurement X-ray CT apparatus configured to irradiate an object placed on a rotating table with X-rays while rotating the object, and reconstruct a projection image of the object to generate a tomographic image of the object. The apparatus includes: a unit configured to generate volume data by performing a CT scan with a spherical calibration jig having a known dimension in contact with the object; a unit configured to obtain a profile of a surface shape of the object in the volume data, and calculate a boundary surface of the spherical calibration jig from center coordinates of the spherical calibration jig; and a unit configured to determine a correction value for adjusting a boundary surface of the object determined from a gradient of the profile to the boundary surface of the spherical calibration jig.

The present invention also solves the foregoing problem by performing measurement using a measurement X-ray CT apparatus configured to irradiate an object placed on a rotating table with X-rays while rotating the object, and reconstruct a projection image of the object to generate a tomographic image of the object. The performing measurement includes: generating volume data by performing a CT scan with a spherical calibration jig having a known dimension in contact with the object; determining a boundary surface of the object by using the correction value determined by the foregoing method; and determining a shape of the object by using the boundary surface.

Here, a database may be generated for each combination of the correction value and a material, the correction value being determined for each normal direction of a measurement surface of the object. In measuring the object, the correction value corresponding to the normal direction of the measurement surface may be read from the database and used for the measurement.

The present invention also solves the foregoing problem by the provision of a measurement apparatus using a measurement X-ray CT apparatus configured to irradiate an object placed on a rotating table with X-rays while rotating the object, and reconstruct a projection image of the object to generate a tomographic image of the object. The measurement apparatus includes: a unit configured to generate volume data by performing a CT scan with a spherical calibration jig having a known dimension in contact with the object; a unit configured to determine a boundary surface of the object by using the collection value determined by the foregoing apparatus for calibrating a measurement X-ray CT apparatus; and a unit configured to determine a shape of the object by using the boundary surface.

Here, the measurement apparatus may further include: a database generated for each combination of the correction value and a material, the correction value being determined for each normal direction of a measurement surface of the object; and a unit configured to read the correction value corresponding to the normal direction of the measurement surface from the database and using the correction value for measurement in measuring the object.

The present invention also solves the foregoing problem by putting an object and a spherical calibration jig having a known dimension in a box transmitting X-rays, generating volume data by performing a CT scan with the spherical calibration jig being in contact with the object in the box, determining a boundary surface of the object by using the correction value determined by the foregoing method, and determining a shape of the object by using the boundary surface.

The present invention also solves the foregoing problem by the provision of: a spherical calibration jig having a known dimension; a box that accommodates the spherical calibration jig and transmits X-rays; a unit configured to generate volume data by performing a CT scan with the spherical calibration jig being in contact with an object in the box; a unit configured to determine a boundary surface of the object by using the correction value determined by the foregoing apparatus for calibrating a measurement X-ray CT apparatus; and a unit configured to determine a shape of the object by using the boundary surface.

The present invention also provides a measurement X-ray CT apparatus including: a spherical calibration jig having a known dimension; a unit configured to generate volume data by performing a CT scan with the spherical calibration jig being in contact with an object; a unit configured to obtain a profile of a surface shape of the object in the volume data; a unit configured to calculate a boundary surface of the spherical calibration jig in the volume data from center coordinates of the spherical calibration jig; a unit configured to correct a boundary surface of the object by using the correction value determined by the foregoing apparatus for calibrating a measurement X-ray CT apparatus; and a unit configured to determine a shape of the object by using the corrected boundary surface.

The measurement X-ray CT apparatus may further include a box that accommodates the object and the spherical calibration jig and transmits the X-rays. The spherical calibration jig can be brought into contact with the object in the box.

Advantageous Effects of Invention

According to the present invention, the precision of measurement X-ray CT can be increased by measuring the spherical calibration jig having a known dimension along with the object to accurately detect the surface shape of the object. High-precision X-ray CT measurement can thus be performed without using a special measuring instrument such as a three-dimensional coordinate measuring machine (CMM).

These and other novel features and advantages of the present invention will become apparent from the following detailed description of preferred embodiments.

BRIEF DESCRIPTION OF DRAWINGS

The preferred embodiments will be described with reference to the drawings, wherein like elements have been denoted throughout the figures with like reference numerals, and wherein.

DESCRIPTION OF EMBODIMENTS

Embodiments of the present invention will be described in detail below with reference to the drawings. It should be noted that the present invention is not limited to the contents described in the following embodiments and practical examples. The components of the embodiments and practical examples described below may include ones easily conceivable by those skilled in the art, substantially identical ones, and ones within the range of equivalency. The components disclosed in the embodiments and practical examples described below may be combined as appropriate, and may be selected and used as appropriate.

Figure 1:
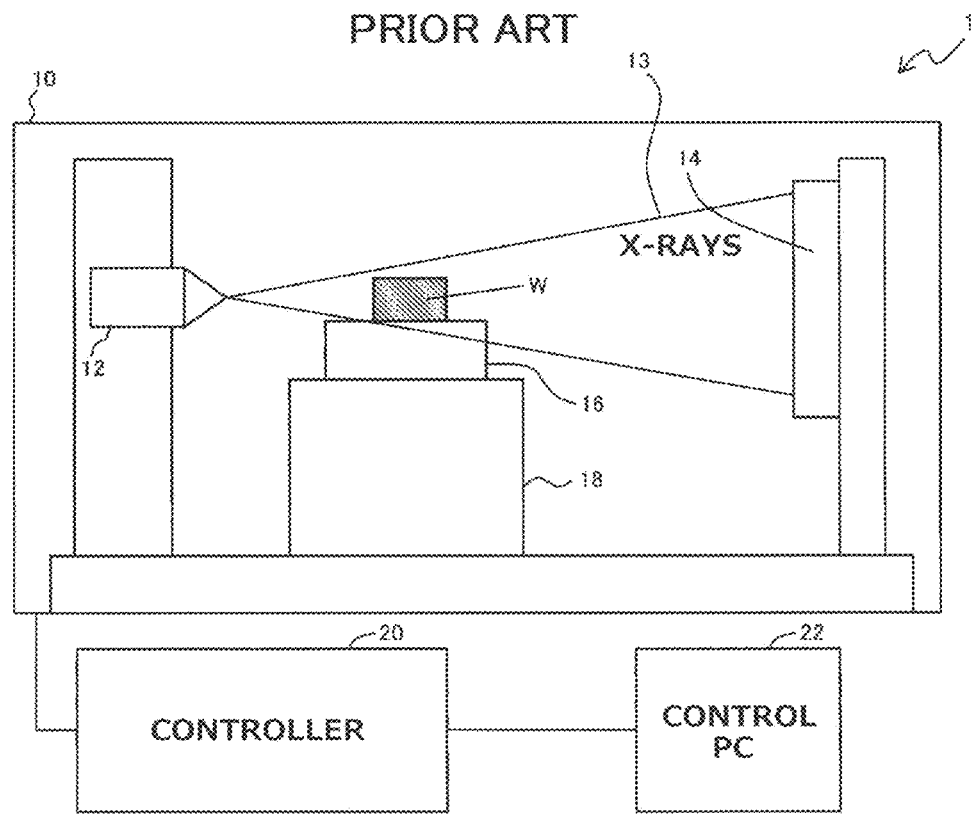
FIG. 1 is a sectional view showing an overall configuration of a typical X-ray CT apparatus used for measurement.
Figure 2:
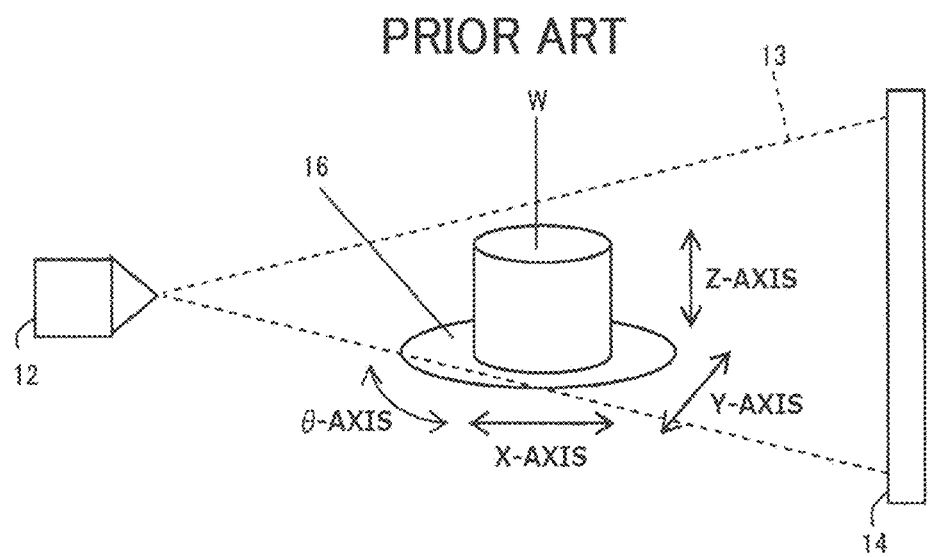
FIG. 2 is a perspective view showing an arrangement of essential parts of the same.
Figure 3:
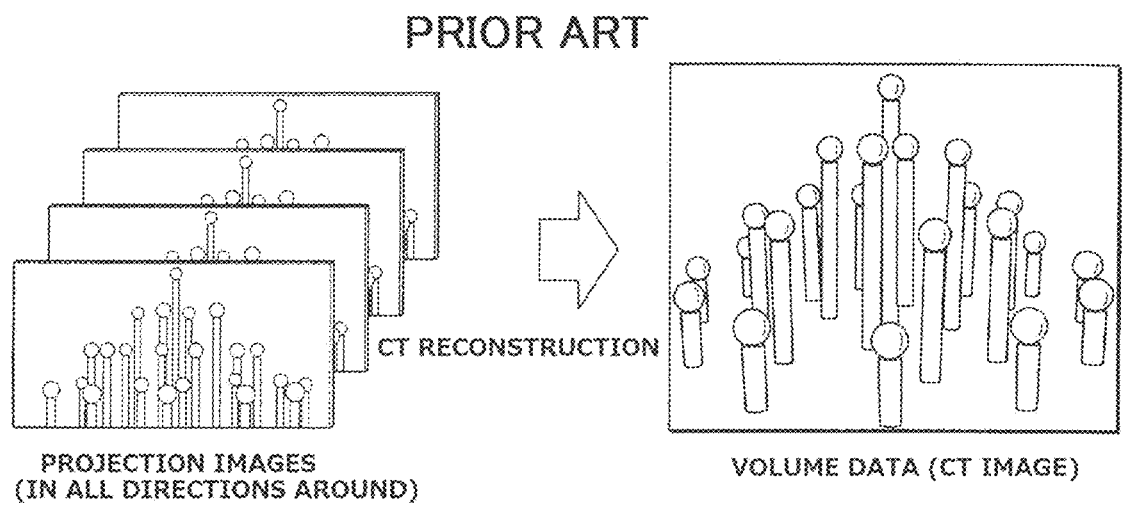
FIG. 3 is a diagram showing how CT reconstruction is performed.
Figure 4:
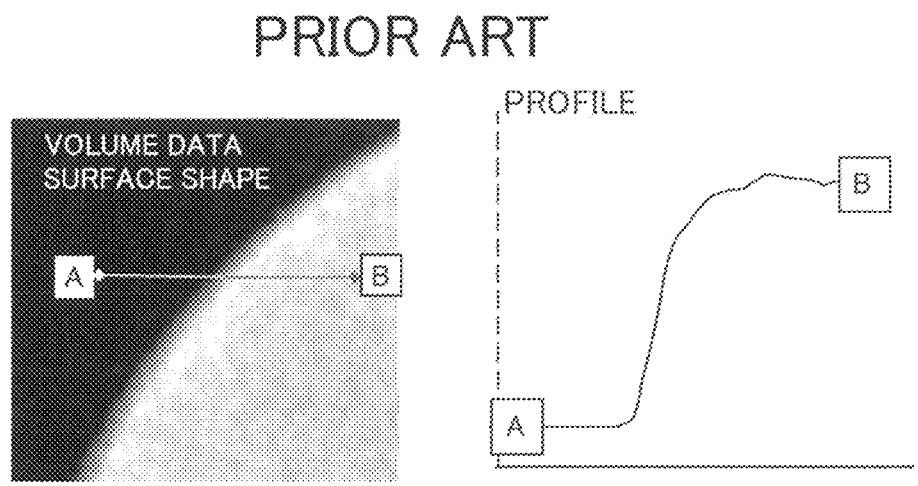
FIG. 4 is a diagram for describing a conventional problem.
Figure 5:
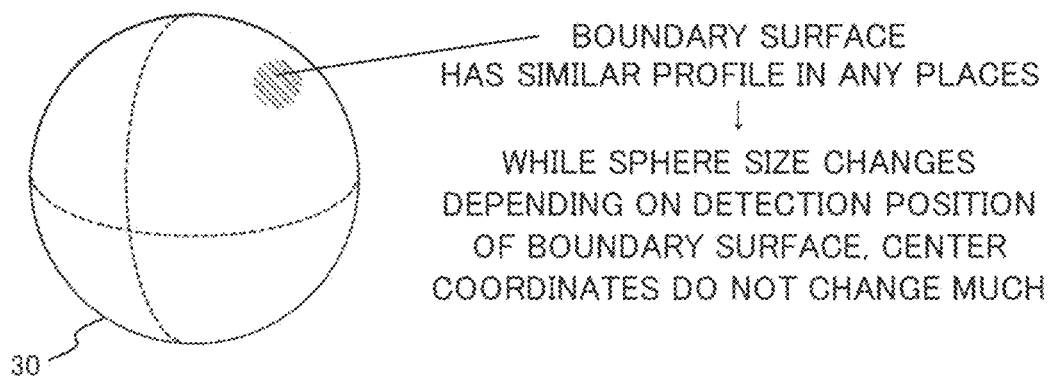
FIG. 5 is a perspective view for describing the principle of the present invention, showing that center coordinates do not change much depending on the detection position of a boundary surface.
Figure 6:
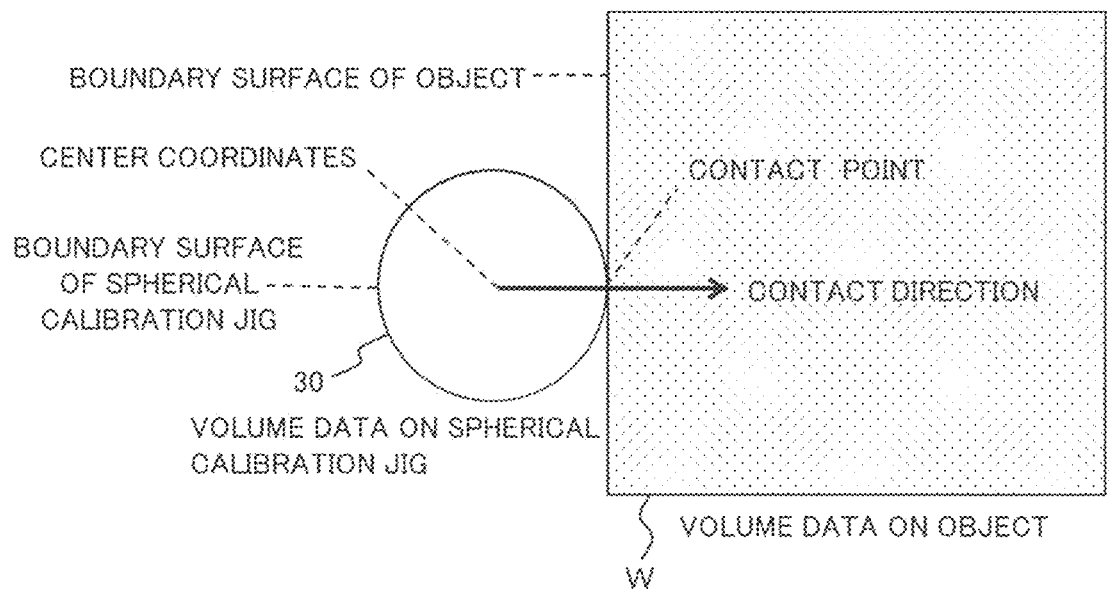
FIG. 6 is a diagram for the same purpose, showing a state of contact between a spherical calibration jig and an object.
Figure 7:
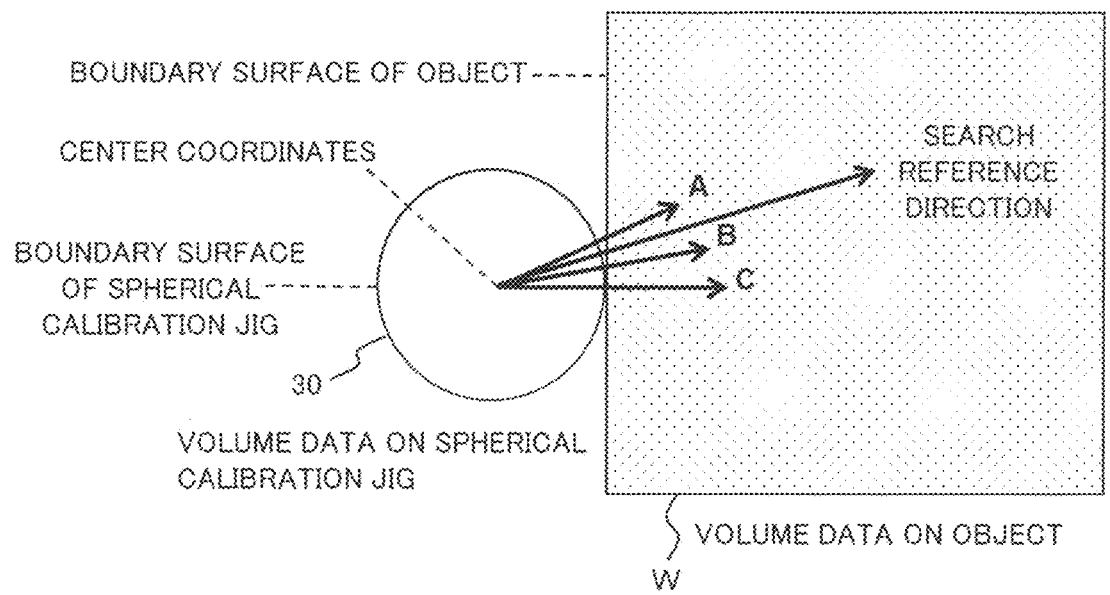
FIG. 7 is a diagram for the same purpose, showing a state where vectors extend in directions slightly shifted from a search reference position.
Figure 8:
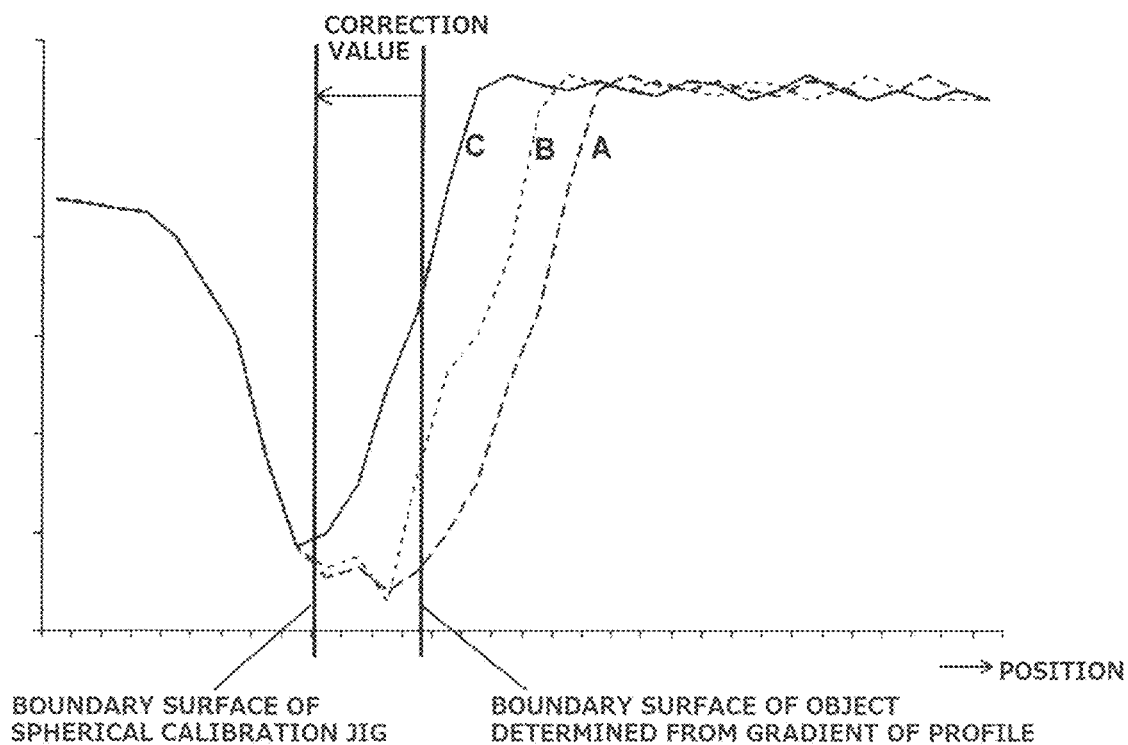
FIG. 8 is a chart for the same purpose, showing an example of a relationship between a boundary surface of the spherical calibration jig and a boundary surface of the object determined from the gradient of a profile.
Figure 9:
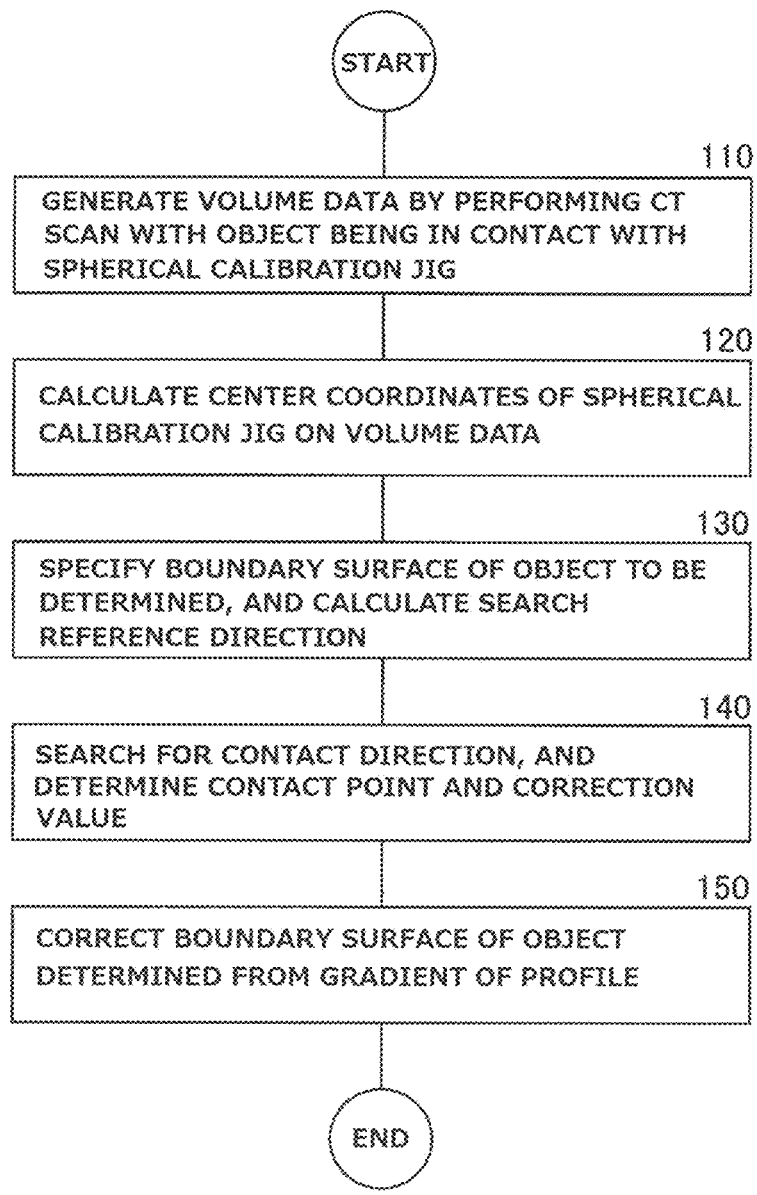
FIG. 9 is a flowchart showing a processing procedure according to a first embodiment of the present invention.

In a first embodiment of the present invention, as shown in FIG. 9, a CT scan is initially performed in step 110 with an object W being in contact with a spherical calibration jig 30. Volume data such as illustrated in FIG. 6 or 7 is thereby generated.

In step 120, the center coordinates of the spherical calibration jig 30 are calculated on the volume data.

In step 130, a boundary surface of the object W to be determined is specified, and a search reference direction is calculated.

In step 140, a contact direction is searched for, and a contact point and a correction value are determined.

In step 150, the boundary surface of the object W determined from the gradient of a profile is corrected.

Since the object W is in contact with the spherical calibration jig 30, the boundary surface of the contact portion can be corrected by the foregoing principle. The corrected boundary surface can be used to calculate the distance of the object W, for example.

Correction values may be determined for respective normal directions of measurement surfaces of the object W, and a database may be generated for each combination of a correction value and a material, for example. In measuring the object W, a correction value corresponding to the normal direction of the measurement surface can be read from the database and used for measurement.

Figure 10:
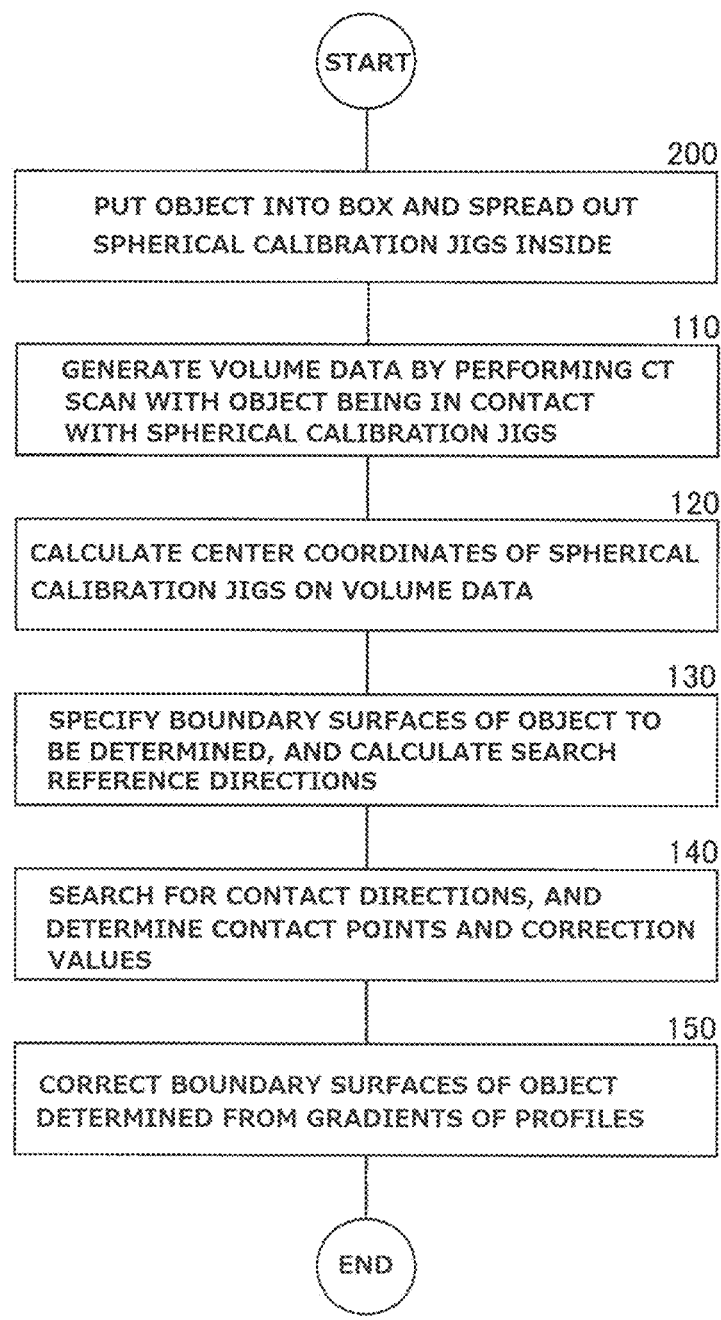
FIG. 10 is a flowchart showing a processing procedure according to a second embodiment of the present invention.

Next, a second embodiment of the present invention will be described with reference to FIG. 10.

Figure 11:
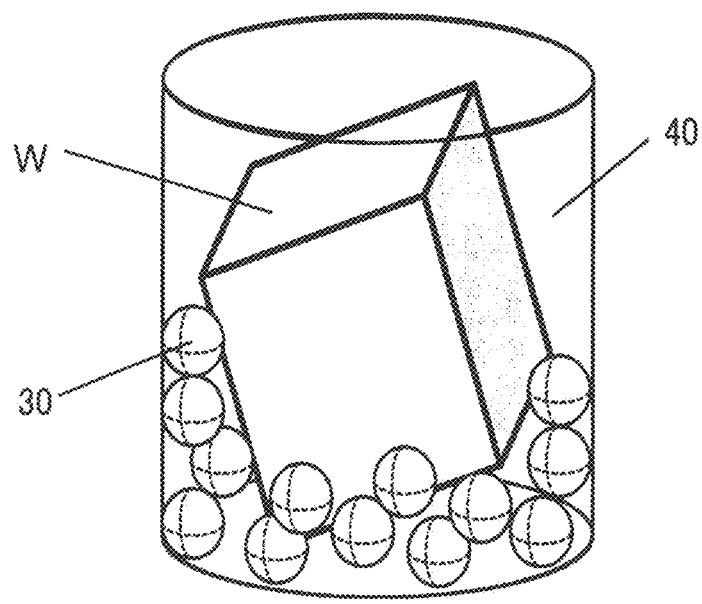
FIG. 11 is a perspective view showing a state where an object and spherical calibration jigs are put in a box made of a material that easily transmits X-rays according to the second embodiment.

In the present embodiment, in step 200, a box 40 made of a material that easily transmits X-rays is initially prepared. As shown in FIG. 11, an object W is put into the box 40 and a plurality of spherical calibration jigs 30 are spread out inside.

Steps 110 to 150 similar to those of the first embodiment are then performed. Note that the number of spherical calibration jigs 30 in steps 110 and 120 is plural.

Figure 12:
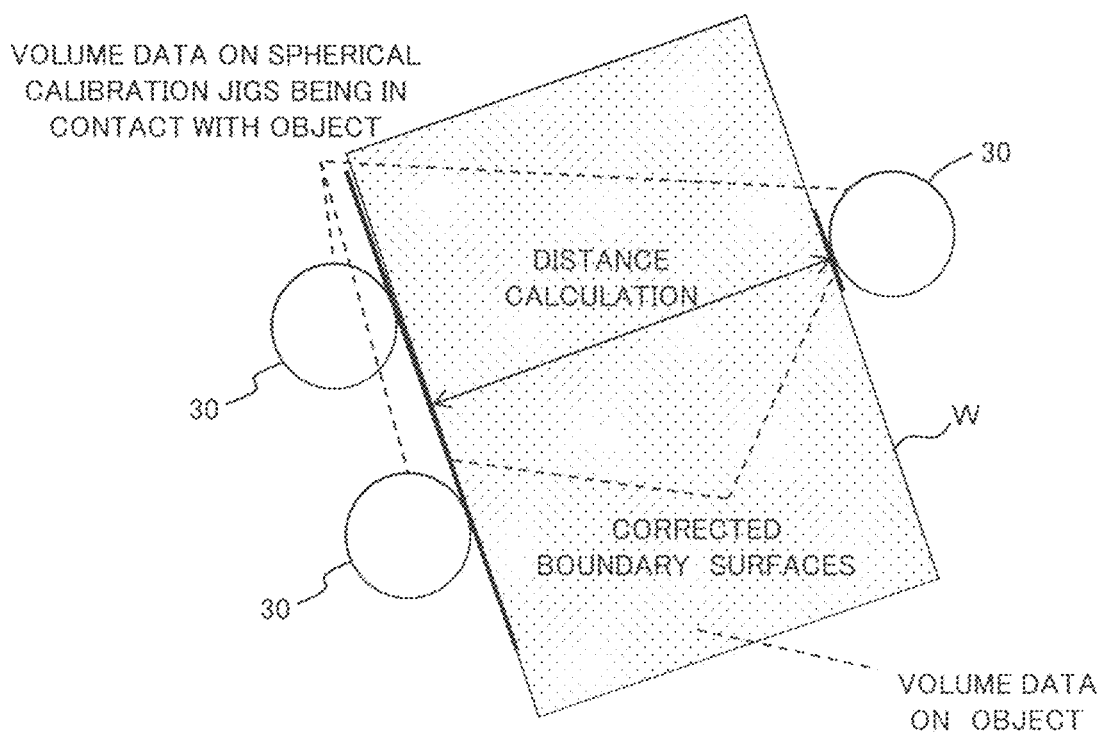
FIG. 12 is a diagram showing an example of a relationship between volume data on spherical calibration jigs being in contact with an object and volume data on the object according to the second embodiment.

In the present embodiment, as illustrated in FIG. 12, the corrected boundary surfaces can be used to calculate a distance of the object W, for example.

The present invention is also applicable to methods other than that of the second embodiment as long as the object W and the spherical calibration jigs 30 can be arranged in contact with each other.

Images can be obtained more easily if the spherical calibration jigs 30 are made of the same material as that of the object W. Different materials, such as brass, aluminum, iron, and ceramic, may be used.

It should be apparent to those skilled in the art that the above-described embodiments are merely illustrative which represent the application of the principles of the present invention. Numerous and varied other arrangements can be readily devised by those skilled in the art without departing from the spirit and the scope of the present invention.

The invention claimed is:

1. A calibration method for a measurement X-ray CT apparatus configured to irradiate an object placed on a rotating table with X-rays while rotating the object, and reconstruct a projection image of the object to generate a tomographic image of the object, the method being implemented by at least a controller including a processor and operably connected to the X-ray CT apparatus, the method comprising:
    performing a CT scan, using an X-ray CT scanner, with a spherical calibration jig having a known dimension and in contact with the object,
    generating, with the processor, volume data from the CT scan with the spherical calibration jig in contact with the object;
    obtaining, with the processor, a profile of a surface shape of the object in the volume data, and calculating a boundary surface of the spherical calibration jig from center coordinates of the spherical calibration jig; and
    determining, with the processor, a correction value for adjusting a boundary surface of the object determined from a gradient of the profile to the boundary surface of the spherical calibration jig.

2. The calibration method for a measurement X-ray CT apparatus according to claim 1, wherein the spherical calibration jig is made of the same material as that of the object.

3. A measurement method using a measurement X-ray CT apparatus configured to irradiate an object placed on a rotating table with X-rays while rotating the object, and reconstruct a projection image of the object to generate a tomographic image of the object, the method being implemented by at least the controller including the processor, the method comprising:
    generating, with the processor, volume data from the CT scan with the spherical calibration jig in contact with the object;
    determining, with the processor, a boundary surface of the object by using the correction value determined by the method according to claim 1; and
    determining, with the processor, a shape of the object by using the boundary surface.

4. The measurement method using a measurement X-ray CT apparatus according to claim 3, wherein a database is generated for each combination of the correction value and a material, the correction value being determined for each normal direction of a measurement surface of the object, and in measuring the object, the correction value corresponding to the normal direction of the measurement surface is read from the database and used for the measurement.

5. A measurement method using a measurement X-ray CT apparatus, the method being implemented by at least a controller including a processor, the method comprising:
    putting an object and a spherical calibration jig having a known dimension in a box transmitting X-rays;
    generating, with the processor, volume data from the CT scan with the spherical calibration jig being in contact with the object in the box;
    determining, with the processor, a boundary surface of the object by using the correction value determined by the method according to claim 1; and
    determining, with the processor, a shape of the object by using the boundary surface.

6. A calibration apparatus for a measurement X-ray CT apparatus configured to irradiate an object placed on a rotating table with X-rays while rotating the object, and reconstruct a projection image of the object to generate a tomographic image of the object, the apparatus comprising an X-ray CT scanner, including a controller with a processor, configured to:
    generate volume data by performing a CT scan with a spherical calibration jig having a known dimension and in contact with the object;
    obtain a profile of a surface shape of the object in the volume data, and calculate a boundary surface of the spherical calibration jig from center coordinates of the spherical calibration jig; and
    determine a correction value for adjusting a boundary surface of the object determined from a gradient of the profile to the boundary surface of the spherical calibration jig.

7. The calibration apparatus for a measurement X-ray CT apparatus according to claim 6, wherein the spherical calibration jig is made of the same material as that of the object.

8. A measurement apparatus using a measurement X-ray CT apparatus configured to irradiate an object placed on a rotating table with X-rays while rotating the object, and reconstruct a projection image of the object to generate a tomographic image of the object, the measurement apparatus comprising the X-ray CT scanner, including the controller including the processor, configured to:
    generate volume data by performing a CT scan with a spherical calibration jig having a known dimension and in contact with the object;
    determine a boundary surface of the object by using the collection value determined by the apparatus according to claim 6; and
    determine a shape of the object by using the boundary surface.

9. The measurement apparatus using a measurement X-ray CT apparatus according to claim 8, further comprising:
- a database generated for each combination of the correction value and a material, the correction value being determined for each normal direction of a measurement surface of the object,
- wherein the X-ray CT scanner, including the controller including the processor, is further configured to read the correction value corresponding to the normal direction of the measurement surface from the database and using the correction value for measurement in measuring the object.

10. A measurement apparatus using a measurement X-ray CT apparatus, comprising:
- a spherical calibration jig having a known dimension;
- a box that accommodates the spherical calibration jig and transmits X-rays;
- the X-ray CT scanner, including the controller including the processor, further configured to:
- generate volume data by performing a CT scan with the spherical calibration jig being in contact with the object in the box;
- determine a boundary surface of the object by using the correction value determined by the apparatus according to claim 6; and
- determine a shape of the object by using the boundary surface.

11. A measurement X-ray CT apparatus comprising:
- a spherical calibration jig having a known dimension; and
- the X-ray CT scanner, including the controller including the processor, further configured to:
- generate volume data by performing a CT scan with the spherical calibration jig being in contact with an object;
- obtain a profile of a surface shape of the object in the volume data;
- calculate a boundary surface of the spherical calibration jig in the volume data from center coordinates of the spherical calibration jig;
- correct a boundary surface of the object by using the correction value determined by the apparatus according to claim 6; and
- determine a shape of the object by using the corrected boundary surface.

12. The measurement X-ray CT apparatus according to claim 11, further comprising a box that accommodates the object and the spherical calibration jig and transmits the X-rays, and wherein the spherical calibration jig is brought into contact with the object in the box.

* * * * *